US009058407B2

(12) United States Patent
Guo

(10) Patent No.: US 9,058,407 B2
(45) Date of Patent: Jun. 16, 2015

(54) PERSISTENT MULTIMEDIA CONTENT VERSIONING

(75) Inventor: Dongbai Guo, Nashua, NH (US)

(73) Assignee: Oracle International Corporation, Redwood Shores, CA (US)

( * ) Notice: Subject to any disclaimer, the term of this patent is extended or adjusted under 35 U.S.C. 154(b) by 1702 days.

(21) Appl. No.: 12/009,750

(22) Filed: Jan. 22, 2008

(65) Prior Publication Data

US 2009/0187610 A1    Jul. 23, 2009

(51) Int. Cl.
*G06F 7/00* (2006.01)
*G06F 17/30* (2006.01)
*G06F 19/00* (2011.01)

(52) U.S. Cl.
CPC ...... *G06F 17/30917* (2013.01); *G06F 17/3028* (2013.01); *G06F 19/327* (2013.01); *G06F 17/30309* (2013.01)

(58) Field of Classification Search
USPC ......... 707/999.1, 999.01, 736, 791, 706, 687, 707/695, 99.101
See application file for complete search history.

(56) References Cited

U.S. PATENT DOCUMENTS

| | | | | |
|---|---|---|---|---|
| 6,671,853 | B1* | 12/2003 | Burkett et al. | 715/235 |
| 7,376,673 | B1* | 5/2008 | Chalecki et al. | 715/223 |
| 2002/0169777 | A1* | 11/2002 | Balajel et al. | 707/10 |
| 2005/0165796 | A1* | 7/2005 | Moore | 707/100 |
| 2005/0165815 | A1* | 7/2005 | Ozzie et al. | 707/100 |
| 2006/0053126 | A1* | 3/2006 | Baca et al. | 707/100 |
| 2006/0184570 | A1* | 8/2006 | Eder | 707/103 R |
| 2007/0088729 | A1* | 4/2007 | Baca et al. | 707/101 |
| 2007/0106647 | A1* | 5/2007 | Schwalb | 707/3 |
| 2008/0162498 | A1* | 7/2008 | Omoigui | 707/10 |
| 2009/0043785 | A1* | 2/2009 | Garward et al. | 707/100 |

\* cited by examiner

*Primary Examiner* — Khanh Pham
*Assistant Examiner* — Eliyah S Harper
(74) *Attorney, Agent, or Firm* — Kraguljac Law Group, LLC

(57) ABSTRACT

Systems, methods, and other embodiments associated with versioned persistent storage of multimedia content in a database object are described. One example method includes controlling a database management system (DBMS) to instantiate a database object that has a binary large object (BLOB) attribute, an XML edits attribute, and a set of metadata attributes. The method includes storing a binary stream associated with a multimedia content (e.g., medical image) in the BLOB attribute and storing an editing history of the set of metadata attributes as a set of edit entries in the XML edits attribute. The method also includes controlling the DBMS to store the database object in a column in a table in a relational database managed by the DBMS.

31 Claims, 10 Drawing Sheets

PERSISTENT MULTIMEDIA CONTENT VERSIONING

COPYRIGHT NOTICE

A portion of the disclosure of this patent document contains material subject to copyright protection. The copyright owner has no objection to the facsimile reproduction of the patent document or the patent disclosure as it appears in the Patent and Trademark Office patent file or records, but otherwise reserves all copyright rights whatsoever.

BACKGROUND

Medical images (e.g., Magnetic Resonance Imaging (MRI) image) are large. A comparably very small amount of metadata often describes a medical image. The metadata may include, for example an image name, a date acquired, a patient name, a patient identifier, an image size, a billing code, and so on. Once recorded, medical images tend to change relatively infrequently, if at all, as compared to the metadata describing these images. However, changes to metadata may typically have lead to duplication of related medical images, yielding tremendous wastage of computing resources. Similar issues apply to other types of multimedia content (e.g., movies, slide shows).

Conventionally, media databases have managed collections of multimedia content and metadata columns by separating the two items. For example, some medical imaging manufacturers follow the DICOM (Digital Imaging and Communication in Medicine) standard (available at [http://medical.nema.org/dicom/2007/]) for versioning support. This standard requires storing separate copies of the edited medical images. The metadata may typically have been stored in a media content table while the actual image data may have been stored externally in external file storage. Pointers in a media content table may have provided indirect access to the externally stored image files. Conventionally, it has been possible to query the metadata columns in the media content table to acquire pointers to actual files stored in external file storage. Unfortunately, this configuration has had issues with synchronization between metadata and image data, transaction control, security, auditing, backup processing, restoration processing, replication, high availability, versioning, and so on. These issues may have arisen because it is relatively inexpensive (e.g., in time, in resources, in computational complexity) to change a relational database column but relatively expensive to propagate a change to external file storage. Thus, it may have been easy to change metadata but difficult to propagate the change to an image stored in external file storage. Separating the metadata from the image data negatively impacts the features (e.g., versioning) provided by storing things in databases.

To understand an issue with the separated architecture, consider a media query directed at media stored in an external file storage. The media query may be processed by a middle tier that performs query mapping so that a query can be made against metadata stored in a media content table. The metadata acquired in response to this first action can then be used to make a query against an external file where the media data is stored. An assembly process may then be required in the middle tier to associate the initially retrieved metadata with the ultimately retrieved media data. Recall that metadata can easily get out of synchronization with media data, which may yield a complicated, resource-intensive, and not provably correct assembly process for example, when the ordering of DICOM attributes do not follow the DICOM standard (e.g., ascending). These issues may arise in the separated architecture since metadata may be stored as traditional relational database columns with a single version and no update history. In some examples, a single flag may be maintained to indicate whether a metadata modification occurred. When this flag indicates that a metadata change occurred, an entire media (or its header) may be reassembled.

Multimedia content is becoming ubiquitous. Database management systems are now used to store this type of digital media. Some conventional systems process multimedia content by encoding it as a binary stream and then persistently storing the binary stream in a binary large object (BLOB). Some conventional systems may facilitate editing metadata associated with multimedia content. These conventional systems may persistently store and manage the metadata separately from the multimedia content. While the metadata may be retrieved for purposes including querying, auditing, assembling a version, and so on, these conventional systems have drawbacks due to the separate storage. For example, conventional systems are typically inefficient with respect to versioning associated with the metadata edits, if they provide any versioning at all. For example, one conventional system may store the multimedia content as a BLOB and may separately store metadata about the BLOB. However, when changes are made to the metadata, the conventional system may replicate the entire object, including the multimedia content and the metadata attributes, even though only the metadata attributes were changed. Thus, conventional multimedia storage systems may save multiple copies of the same complete multimedia content, which can lead to significant wastage of storage. Additionally, changes to metadata may not be directly independently accessible. For example, accessing the changes to metadata may require accessing an entire BLOB and/or multiple versions of a BLOB.

BRIEF DESCRIPTION OF THE DRAWINGS

The accompanying drawings, which are incorporated in and constitute a part of the specification, illustrate various example systems, methods, and other example embodiments of various aspects of the invention. It will be appreciated that the illustrated element boundaries (e.g., boxes, groups of boxes, or other shapes) in the figures represent one example of the boundaries. One of ordinary skill in the art will appreciate that in some examples one element may be designed as multiple elements or that multiple elements may be designed as one element. In some examples, an element shown as an internal component of another element may be implemented as an external component and vice versa. Furthermore, elements may not be drawn to scale.

DETAILED DESCRIPTION

Figure 1:
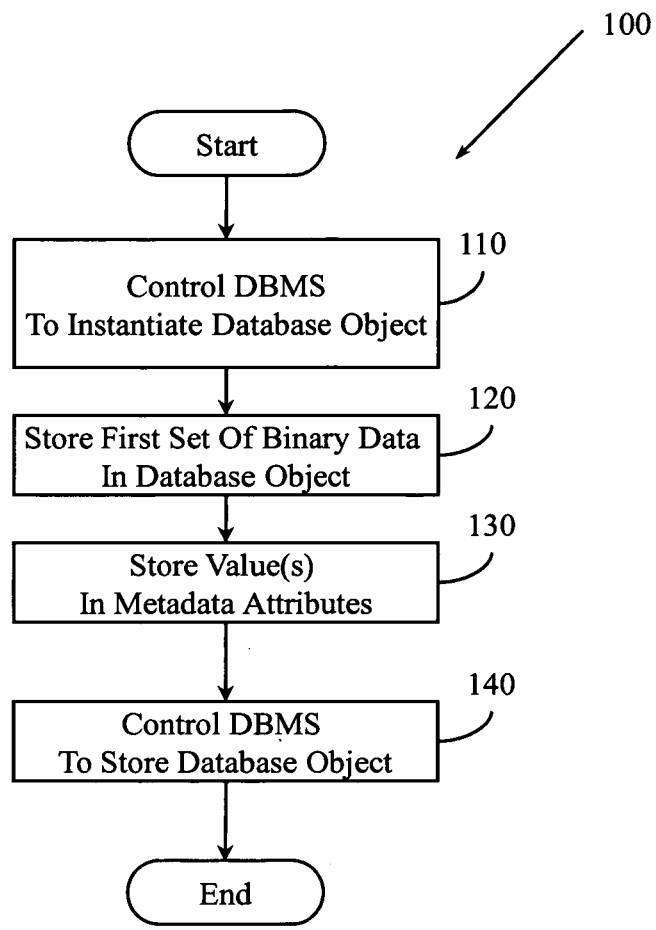
FIG. 1 illustrates an example method associated with persistent multimedia content storage with versioning.

Example systems and methods use persistent database objects to store and manage both multimedia content and metadata editing history. Both the multimedia content, which may be encoded as a binary stream, and the metadata, are stored in a single object. This differs from conventional solutions that store binary data and metadata separately. In one example, an entire persistent database object having media content, metadata attributes, and a metadata change attribute can be stored in a single database column. Thus, versioning of the multimedia content associated with the persistent database object can be implemented as an inherent property of the persistent multimedia content. In one example, editing history may be treated as a separate attribute of a database object. In another example, editing history may be treated as part of an object metadata. In another example, editing history may be treated as part of a BLOB (e.g., extension BLOB) that forms part of a database object, and so on.

In one example, a database object may include a BLOB attribute that stores a particular version of a multimedia content. The BLOB may store a binary stream. This may be the "original" binary stream associated with a multimedia content. The database object may also include a document metadata attribute that specifies a metadata editing history. In one example, this attribute may be an XML attribute. This attribute may be constrained by an XML schema. This attribute may by indexed using XMLIndex and thus may be queried using keywords and/or an XPath query. Note that the metadata and its change history are stored in the same object as the content. When the editing history is handled as part of an object metadata, and when the object metadata is handled by an XML attribute, then the editing history may be indexed along with other XML metadata. In one example, the database object may also include a second BLOB attribute (e.g., extension). This second BLOB attribute may store a binary mapping of metadata editing history. This binary mapping facilitates efficient construction of versions of the binary multimedia content using the stored version and the mapping. In one example, an arbitrary version of the binary multimedia content may be constructed without reaching back to an initial version of the multimedia content and then sequentially stepping through intermediate versions of the multimedia content.

The elements and format of the database object facilitate seamlessly combining a change history with other multimedia metadata so that a single set of XML indices can be built for multimedia metadata to query for multimedia content across versions. Versioning information and editing history are distinct concepts. An object may be versioned without editing history. For example, an editing history can be derived from a set of assembly instructions. The editing history derivation could be performed by an external logic. In one example, assembly instructions could be derived at runtime from editing history. In another example, editing history may be persistently stored. Whether editing history is stored may be determined by, for example, a tradeoff made between storage space and processing speed. In one example, both editing history and version information may be stored. Version information may include two parts. A first part may be an assembly instruction that can be stored in an object's XML metadata, in an object's binary data, and so on. A second part may be added binary streams. The added binary streams may be binary streams segments that are not part of the current version of a media object that is stored in a first BLOB attribute in its entirety. The binary streams may be stored in XML as, for example, Base64 binary data, or in the extension BLOB portion of a database object.

In one example, the database object is implemented using an object-relational database technology (e.g., PL/SQL object). Additionally, XML content can be implemented with XML database technology. Stream reading of different multimedia content versions can be implemented with a streaming interface in different programming languages (e.g., C, C++, C#).

The multimedia content may be, for example, a medical image. The metadata associated with such content may make up less than 0.1% of the byte stream associated with the image. Saving an entire duplicate copy of the multimedia content just because one or two bytes of the metadata are edited leads to enormous wastage of space. Thus, example systems and methods facilitate saving metadata and changes to metadata without replicating the associated multimedia content. Binary mappings of the metadata editing history can be stored in the second BLOB attribute to prevent the duplication associated with complete copying and storing. The efficiencies gained by such version control do not come with the additional cost of managing additional objects. Conventionally, a different object may have been created for each version. Instead, example systems and methods may use a single database object to store original multimedia content, associated metadata, and associated metadata editing history. Thus, only a single set of indices is required for both the multimedia content and its editing history. This facilitates keeping index size small which in turn facilitates keeping a query interface simple and efficient.

The metadata attribute of the database object can be thought of as an audit message that can be displayed and reviewed. In one example, the audit message may be user-readable. In one example of the persistent database object, the metadata and its related multimedia content can be retrieved using a single query. The metadata attribute may be indexed with an XML index to allow keyword and/or XPath query.

Differences between multimedia content stored in the first BLOB attribute and another version edited by a user can be pre-computed. In one example, these differences can be stored in the second BLOB attribute. The differences can be retrieved during an assembly process without generating and/or moving binary data since all binary segments are either available in the original media in the first BLOB attributes or are precomputed and stored in the second BLOB attributes. Therefore, the differences and results from two or more BLOBs can be accessed at runtime without moving and/or copying binary data. This reduces overhead associated with providing a version of a multimedia content or a version of an object when compared to conventional systems.

Some applications (e.g., healthcare) require unique identities for multimedia contents. The unique identity can be stored in a metadata attribute associated with the database object and thus can be accessed, queried, indexed, versioned, and so on, similar to how other metadata attributes are processed. In a system where multiple versions of the same DICOM object coexists, the multiple versions may be accessed through different identifiers managed by the same database object. Conventional systems may have stored the identity in a different object, which may therefore have required multiple indices and a complex query interface. These multiple indices and complex query interface would then be employed during a lengthy run-time assembly that, hopefully, would recreate the desired content and associate it with the desired identity. Unfortunately, the metadata and its related multimedia content frequently lost synchronization.

The following includes definitions of selected terms employed herein. The definitions include various examples and/or forms of components that fall within the scope of a term and that may be used for implementation. The examples are not intended to be limiting. Both singular and plural forms of terms may be within the definitions.

References to "one embodiment", "an embodiment", "one example", "an example", and so on, indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

ASIC: application specific integrated circuit.
CD: compact disk.
CD-R: CD recordable.
CD-RW: CD rewriteable.
DVD: digital versatile disk and/or digital video disk.
HTTP: hypertext transfer protocol.
LAN: local area network.
PCI: peripheral component interconnect.
PCIE: PCI express.
RAM: random access memory.
DRAM: dynamic RAM.
SRAM: synchronous RAM.
ROM: read only memory.
PROM: programmable ROM.
EPROM: erasable PROM.
EEPROM: electrically erasable PROM.
SQL: structured query language.
OQL: object query language.
USB: universal serial bus.
XML: extensible markup language.
WAN: wide area network.

XLink describes connections between documents. XLink provides an attribute-based syntax for attaching links to documents. XLink provides an XML syntax for describing directed graphs in which the vertices are documents at particular URIs and the edges are links between the documents. A simple link defines a one-way connection between two resources, the source (e.g., starting resource) is the link element while the target (e.g., ending resource) is identified by a URI. XLinks use locators and arcs. Each locator element has an xlink:type attribute associated with the value locator and an xlink:href attribute containing a URI for the resource it locates. Arcs are paths between resources. Linkbases are XML documents that contain inbound or third-party links. A linkbase may establish links from documents other than the linkbase itself.

XML refers to extensible markup language. XML is a document format, a meta-markup language for text documents. XML documents are trees that start at a root. XML documents include elements. An element can be defined generically and have a particular instance(s). An instance of an element has "content" (e.g., a value(s)). XML elements can have attributes. An attribute is a name-value pair attached to the element start tag. XML Schemas describe allowed content of XML documents conforming to a particular XML vocabulary.

XPath is a non-XML language used to identify particular parts of XML documents. XPath indicates nodes by position, relative position, type, content, and so on. XPath expressions may represent numbers, strings, Booleans, and so on. XPath is a language for picking nodes and sets of nodes out of the tree structure that is an XML document.

XPointer uses XPath expressions to identify the particular point in or part of an XML document to which an XLink links. XPointer addresses individual parts of an XML document.

XSL equals extensible stylesheet language. XSL include XSL transformations and XSL formatting objects.

XSLT equals XSL transformations. XSLT is an XML application that specifies rules by which one XML document is transferred into another. XSLT is a general purpose language for transforming one XML document into another for purposes including, for example, web page display. An XSLT stylesheet contains templates that control what output is created from what input. An element has a "match" attribute that contains an XPath pattern identifying the input it matches. XSLT uses XPath expressions to match and select particular elements in an input document for copying into an output document or for further processing.

"Computer component", as used herein, refers to a computer-related entity (e.g., hardware, firmware, software in execution, combinations thereof). Computer components may include, for example, a process running on a processor, a processor, an object, an executable, a thread of execution, and a computer. A computer component(s) may reside within a process and/or thread. A computer component may be localized on one computer and/or may be distributed between multiple computers.

"Computer communication", as used herein, refers to a communication between computing devices (e.g., computer, personal digital assistant, cellular telephone) and can be, for example, a network transfer, a file transfer, an applet transfer, an email, an HTTP transfer, and so on. A computer communication can occur across, for example, a wireless system (e.g., IEEE 802.11), an Ethernet system (e.g., IEEE 802.3), a token ring system (e.g., IEEE 802.5), a LAN, a WAN, a point-to-point system, a circuit switching system, a packet switching system, and so on.

"Computer-readable medium", as used herein, refers to a medium that stores signals, instructions and/or data. A computer-readable medium may take forms, including, but not limited to, non-volatile media, and volatile media. Non-volatile media may include, for example, optical disks, magnetic disks, and so on. Volatile media may include, for example, semiconductor memories, dynamic memory, and so on. Common forms of a computer-readable medium may include, but are not limited to, a floppy disk, a flexible disk, a hard disk, a magnetic tape, other magnetic medium, an ASIC, a CD, other optical medium, a RAM, a ROM, a memory chip or card, a memory stick, and other media from which a computer, a processor or other electronic device can read.

In some examples, "database" is used to refer to a table. In other examples, "database" may be used to refer to a set of tables. In still other examples, "database" may refer to a set of data stores and methods for accessing and/or manipulating those data stores.

"Data store", as used herein, refers to a physical and/or logical entity that can store data. A data store may be, for example, a database, a table, a file, a list, a queue, a heap, a memory, a register, and so on. In different examples, a data store may reside in one logical and/or physical entity and/or may be distributed between two or more logical and/or physical entities.

"Logic", as used herein, includes but is not limited to hardware, firmware, software in execution on a machine, and/or combinations of each to perform a function(s) or an action(s), and/or to cause a function or action from another logic, method, and/or system. Logic may include a software controlled microprocessor, a discrete logic (e.g., ASIC), an analog circuit, a digital circuit, a programmed logic device, a memory device containing instructions, and so on. Logic may include one or more gates, combinations of gates, or other circuit components. Where multiple logical logics are described, it may be possible to incorporate the multiple logical logics into one physical logic. Similarly, where a single logical logic is described, it may be possible to distribute that single logical logic between multiple physical logics.

An "operable connection", or a connection by which entities are "operably connected", is one in which signals, physical communications, and/or logical communications may be sent and/or received. An operable connection may include a physical interface, an electrical interface, and/or a data interface. An operable connection may include differing combinations of interfaces and/or connections sufficient to allow operable control. For example, two entities can be operably connected to communicate signals to each other directly or through one or more intermediate entities (e.g., processor, operating system, logic, software). Logical and/or physical communication channels can be used to create an operable connection.

"Query", as used herein, refers to a semantic construction that facilitates gathering and processing information. A query may be formulated in a database query language (e.g., SQL), an OQL, a natural language, and so on.

"Signal", as used herein, includes but is not limited to, electrical signals, optical signals, analog signals, digital signals, data, computer instructions, processor instructions, messages, a bit, a bit stream, or other means that can be received, transmitted and/or detected.

"Software", as used herein, includes but is not limited to, one or more executable instructions that cause a computer, processor, or other electronic device to perform functions, actions and/or behave in a desired manner. "Software" does not refer to stored instructions being claimed as stored instructions per se (e.g., a program listing). The instructions may be embodied in various forms including routines, algorithms, modules, methods, threads, and/or programs including separate applications or code from dynamically linked libraries.

"User", as used herein, includes but is not limited to one or more persons, software, computers or other devices, or combinations of these.

Some portions of the detailed descriptions that follow are presented in terms of algorithms and symbolic representations of operations on data bits within a memory. These algorithmic descriptions and representations are used by those skilled in the art to convey the substance of their work to others. An algorithm, here and generally, is conceived to be a sequence of operations that produce a result. The operations may include physical manipulations of physical quantities. Usually, though not necessarily, the physical quantities take the form of electrical or magnetic signals capable of being stored, transferred, combined, compared, and otherwise manipulated in a logic, and so on. The physical manipulations create a concrete, tangible, useful, real-world result.

It has proven convenient at times, principally for reasons of common usage, to refer to these signals as bits, values, elements, symbols, characters, terms, numbers, and so on. It should be borne in mind, however, that these and similar terms are to be associated with the appropriate physical quantities and are merely convenient labels applied to these quantities. Unless specifically stated otherwise, it is appreciated that throughout the description, terms including processing, computing, determining, and so on, refer to actions and processes of a computer system, logic, processor, or similar electronic device that manipulates and transforms data represented as physical (electronic) quantities.

Example methods may be better appreciated with reference to flow diagrams. While for purposes of simplicity of explanation, the illustrated methodologies are shown and described as a series of blocks, it is to be appreciated that the methodologies are not limited by the order of the blocks, as some blocks can occur in different orders and/or concurrently with other blocks from that shown and described. Moreover, less than all the illustrated blocks may be required to implement an example methodology. Blocks may be combined or separated into multiple components. Furthermore, additional and/or alternative methodologies can employ additional, not illustrated blocks.

FIG. 1 illustrates a method 100 associated with providing persistent multimedia content versioning. Method 100 may include, at 110, controlling a database management system (DBMS) to instantiate a database object. Controlling the DBMS may include providing a signal to the DBMS, invoking a method in the DBMS, providing data through an application programming interface (API) associated with the DBMS, and so on. The database object may include a first binary large object (BLOB) attribute, an XML edits attribute, and a set of metadata attributes. In one example the database object is a PL/SQL object.

Method 100 may also include, at 120, storing a first set of binary data associated with a multimedia content in the first BLOB attribute. The multimedia content may be, for example, a medical image, a movie, a slide show, and so on.

Method 100 may also include, at 130, storing a value(s) in the set of metadata attributes. The metadata attributes may be configured to store information associated with the multimedia content and/or the database object. Thus, the metadata attributes may store information including, but not limited to, a content name, a content size, a content creation date, a content source, a patient name, a patient identifier, an encoding format, a billing code, and so on.

Method 100 may also include, at 140, controlling the DBMS to store the database object in a column in a table in a relational database managed by the DBMS. Note that the database object includes both the media content, XML attributes describing the content and/or object, and an XML edits attribute in which edits to the metadata can be stored. Thus, the media, its attributes, and its edits may be stored in a single database object in a single database column.

While FIG. 1 illustrates various actions occurring in serial, it is to be appreciated that various actions illustrated in FIG. 1 could occur substantially in parallel. By way of illustration, a first process could control the DBMS to instantiate and store objects, a second process could store binary data, and a third process could store values in the metadata attributes. While three processes are described, it is to be appreciated that a greater and/or lesser number of processes could be employed and that lightweight processes, regular processes, threads, and other approaches could be employed.

In one example, a method may be implemented as computer executable instructions. Thus, in one example, a computer-readable medium may store computer executable instructions that if executed by a machine (e.g., processor) cause the machine to perform method 100. While executable instructions associated with the method 100 are described as being stored on a computer-readable medium, it is to be appreciated that executable instructions associated with other example methods described herein may also be stored on a computer-readable medium.

Figure 2:
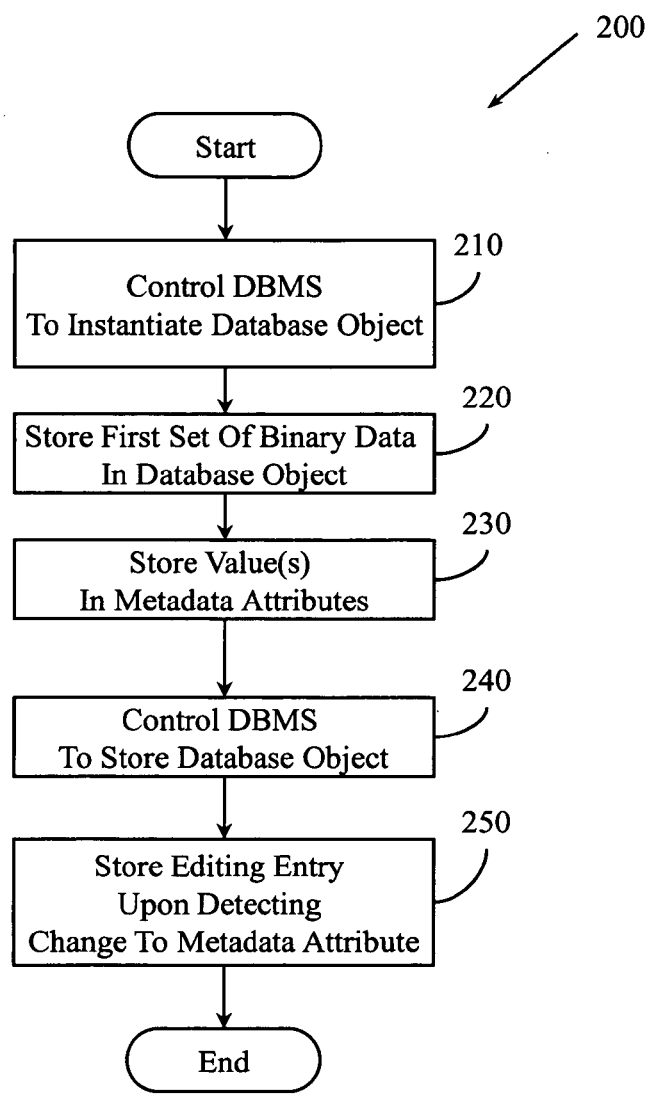
FIG. 2 illustrates another example method associated with persistent multimedia content storage with versioning.

FIG. 2 illustrates a method 200 that includes several actions similar to those described in connection with method 100 (FIG. 1). For example, method 200 includes controlling a DBMS at 210 to instantiate a database object, storing binary data at 220, storing values in the metadata attributes at 230, and controlling the DBMS to store the database object at 240. However, method 200 includes an additional action.

For example, method 200 includes, at 250, storing in the XML edits attribute an editing entry associated with the set of metadata attributes. The storing at 250 may be performed upon determining that a member of the set of metadata attributes was changed. Changes may take different forms and thus the editing entry is to describe a change to the member of the set of metadata attributes. In one example, the editing entry may be a human-readable XML attribute.

In one example, the editing entry may describe a deletion from the set of metadata attributes. In another example, the editing entry may describe a deletion from the first set of binary data. The deletion may be associated with, for example, cropping an image. Thus, in one example, not only is versioning available for the more common situation of metadata deletions, but also for the less frequent situation of media deletions. Deletions are only one type of edit that metadata attributes and/or media may experience. Therefore, in one example, the editing entry may include an addition to the set of metadata attributes and/or an update to the set of metadata attributes. The update may change an existing value while an addition may insert a completely new attribute. Thus, method 200 facilitates providing forward compatibility for previously stored media by allowing the addition of new metadata attributes. As described above, in some cases the media itself may change. Thus, in one example, the editing entry may include an addition to the first set of binary data, and/or an update to the first set of binary data. These changes may be the result, for example, of a retouching of the media content. For example, a first medical image may include artifacts associated with motion that occurred during imaging. The first medical image may subsequently be retouched to remove and/or lessen the artifacts. Rather than store a completely new copy of the medical image, method 200 facilitates storing edits for reproducing a copy.

Figure 3:
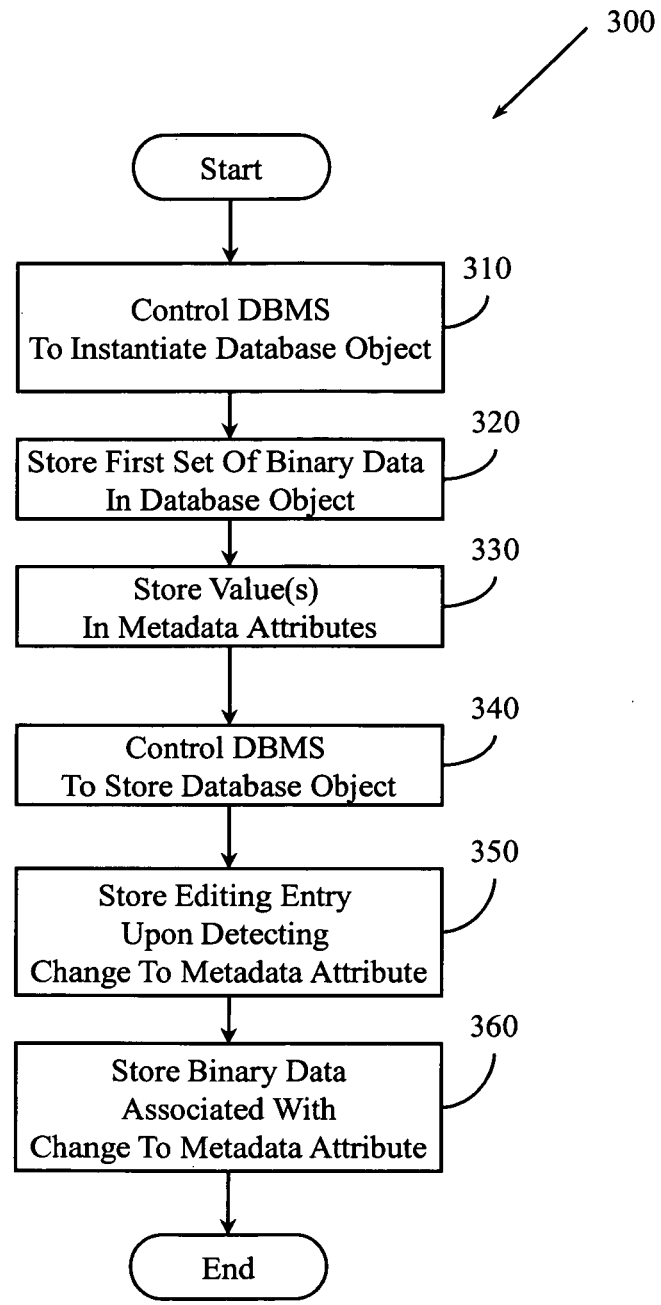
FIG. 3 illustrates another example method associated with persistent multimedia content storage with versioning.

FIG. 3 illustrates a method 300 that includes several actions similar to those described in connection with method 200 (FIG. 2). For example, method 300 includes controlling a DBMS at 310 to instantiate a database object, storing binary data at 320, storing values in the metadata attributes at 330, controlling the DBMS to store the database object at 340, and storing an edit entry at 350. However, method 300 includes an additional action.

The additional action concerns a second BLOB attribute in the database object. The second BLOB attribute may store a second set of binary data associated with a binary mapping of a change to a member of the set of metadata attributes. Thus, the instantiating at 310 and the storing at 340 may concern an object that includes the second BLOB attribute along with the first BLOB attribute, the metadata, and the XML edits attribute.

Method 300 includes, at 360, storing in the second BLOB attribute a set of binary data associated with an addition to the set of metadata attributes and/or and a set of binary data associated with an update to the set of metadata attributes. The differences between a first version of the set of metadata attributes and a second different version of the set of metadata attributes may be pre-computed and thus the storing at 360 may include storing the difference as a set of binary data in the second BLOB attribute. Similarly, a binary mapping associated with an edit entry in the XML edits attribute may be computed. Thus, the storing at 360 may include storing the binary mapping as a set of binary data in the second BLOB attribute.

In one example, the second set of binary data may also be associated with a binary mapping of a change to the first set of binary data. In one example, the storing at 360 may include storing in the second BLOB attribute a set of binary data associated with an addition to the first set of binary data and/or a set of binary data associated with an update to the first set of binary data. This is a less frequent occurrence.

Figure 4:
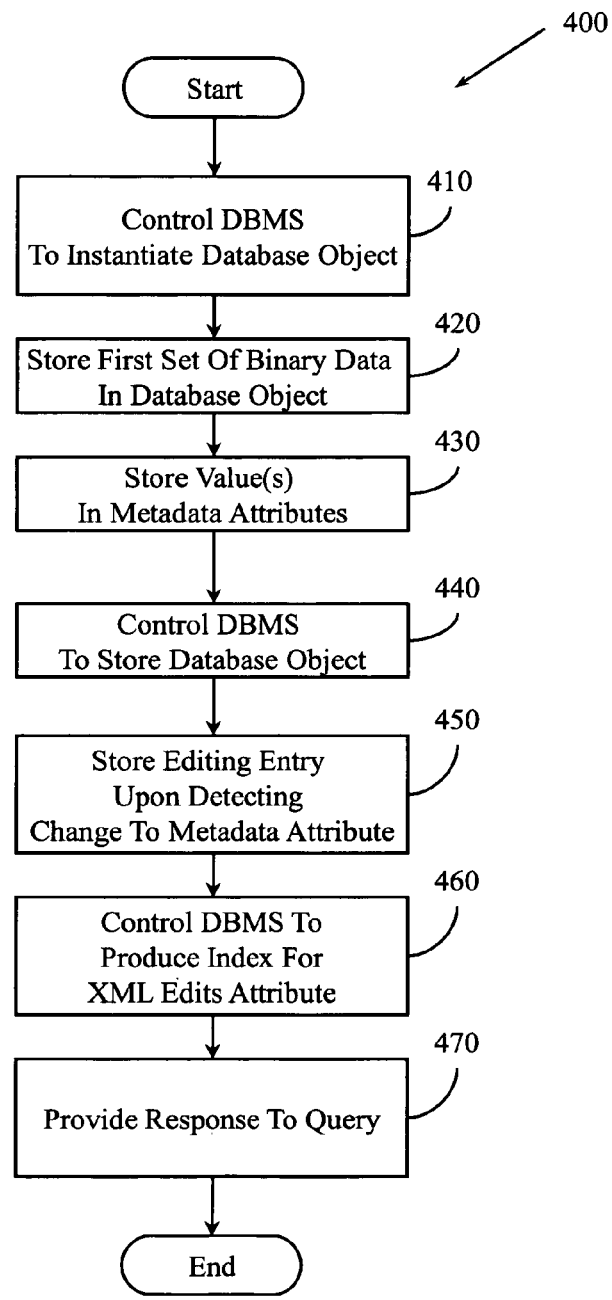
FIG. 4 illustrates another example method associated with persistent multimedia content storage with versioning.

FIG. 4 illustrates a method 400 that includes several actions similar to those described in connection with method 300 (FIG. 3). For example, method 400 includes controlling a DBMS at 410 to instantiate a database object, storing binary data at 420, storing values in the metadata attributes at 430, controlling the DBMS to store the database object at 440, and storing an edit entry at 450. However, method 400 includes additional actions concerning indexing the XML edits attribute.

Method 400 includes, at 460, controlling the DBMS to produce an index for the XML edits attribute. Controlling the DBMS may include, for example, controlling the DBMS to produce an index on XML content. With an index available, method 400 may accept queries. Therefore, method 400 may include, at 470, providing a result to a keyword query directed at the XML edits attribute. Providing the result at 470 may also include providing a result to an XPATH query directed at the XML edits attribute. In either case, the result is based, at least in part, on the index created in response to controlling the DBMS at 460.

Figure 5:
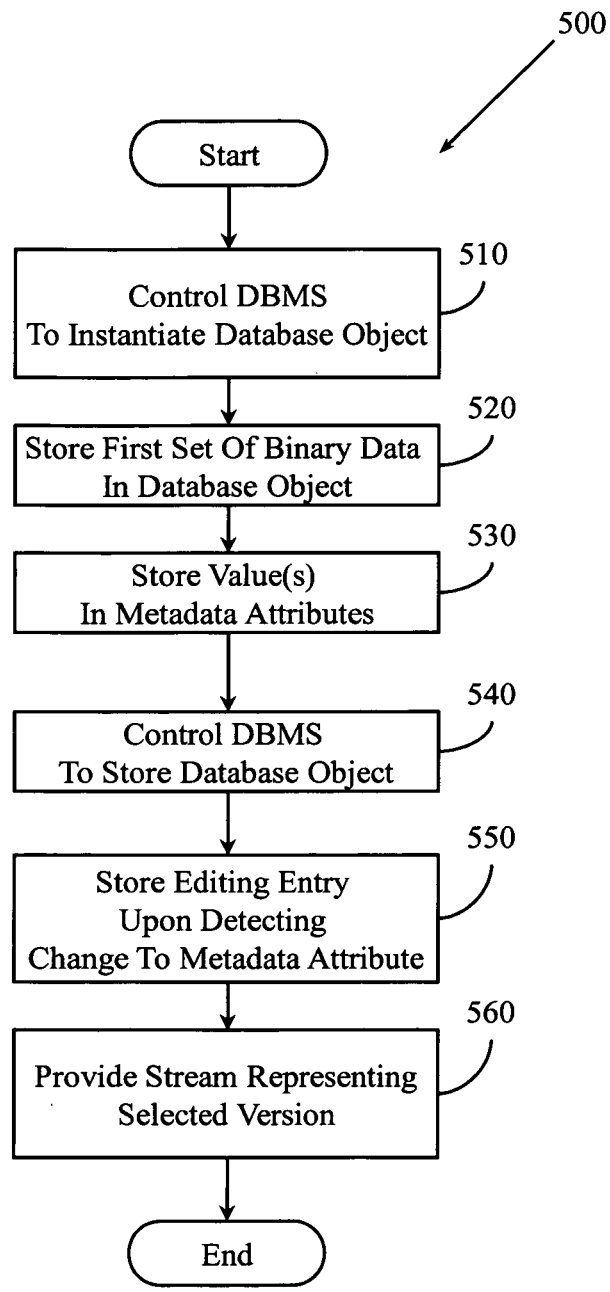
FIG. 5 illustrates another example method associated with persistent multimedia content storage with versioning.

FIG. 5 illustrates a method 500 that includes several actions similar to those described in connection with method 300 (FIG. 3). For example, method 500 includes controlling a DBMS at 510 to instantiate a database object, storing binary data at 520, storing values in the metadata attributes at 530, controlling the DBMS to store the database object at 540, and storing an edit entry at 550. However, method 500 includes an additional action.

Method 500 includes, at 560, providing a binary stream that represents a selected version of the database object. The binary stream may be built from the first set of binary data, the set of metadata attributes, and the XML edits attribute. In one example, providing the binary stream includes computing $BLOB(I+K)=BLOB(I)-U(I,K)+M(I,K)$;

where $BLOB(I)$ is the I-th version of the first set of binary data;

where $U(I,K)$ represents a complete set of metadata attributes to be deleted from I-th version of the database object; and where $M(I,K)$ represents a complete set of metadata attributes to be added to the I-th version of the database object.

In another example, edits to both the metadata and the image data may be considered. Therefore, providing the binary stream at 560 may include computing $BLOB_{complete}(I+K)=BLOB_{complete}(I)-U_{complete}(I,K)+M_{complete}(I,K)$;

where $BLOB_{complete}(I)$ is the I-th version of the first set of binary data;

where $U_{complete}(I,K)$ represents a complete set of metadata attributes to be deleted from I-th version of the database object and a complete set of deletions from the I-th version of the first set of binary data; and where $M_{complete}(I,K)$ represents a complete set of metadata attributes to be added to the I-th version of the database object and a complete set of additions to the I-th version of the first set of binary data.

In one example, data structures may be constructed that facilitate storing data on a computer-readable medium and/or in a data store. The data structure may be an object, where "object" is used in its computer-science term-of art form. Thus, the object may include data and methods for manipulating that data. Thus, in one example, a computer-readable medium may store an object that includes a first storage area containing data representing a medical image. While a medical image is described, more generally the first storage area could store a set of binary data associated with a multimedia content. The object may also include a second storage area containing metadata describing the medical image, and a third storage area containing edits to the metadata. In one example, a selected version of the object may be synthesized from the data representing the medical image, the metadata, and the edits to the metadata. While three storage areas are described, it is to be appreciated that a greater and/or lesser number of areas could be employed. Additionally, it is to be appreciated that other objects produced by the example systems and methods described herein may be encoded onto a computer-readable medium.

FIGS. 1 through 5 illustrate methods 100 through 500. One skilled in the art will appreciate that other methods that manipulate other database object instances may be performed to facilitate persistent multimedia content versioning. One example method may include controlling a DBMS to instantiate a database object that includes a first BLOB attribute and a versions attribute. This example method may also include storing a first set of binary data associated with a multimedia content in the first BLOB attribute and storing a value(s) in the versions attribute. The values stored in the versions attribute may be associated with the multimedia content and/or the database object. The example method may also include controlling the DBMS to store the database object in a column in a table in a relational database managed by the DBMS.

The versions attribute may store information useful for assembling a version of a media content. Thus, in one example, the versions attribute may store an assembly instruction(s) from which a version of the binary object can be computed. The assembly instructions may include a delete instruction that identifies a segment of the binary data associated with the multimedia content to be excluded from a version. The assembly instructions may also include an addition instruction that identifies a segment of binary data to be added to the binary data associated with the multimedia content. The assembly instructions may also include a copy instruction that identifies a segment of binary data to be copied from the binary data associated with the multimedia content when a version of the multimedia content is assembled.

In one example, the method may include controlling the DBMS to store binary streams to be added to the database object. The binary streams are stored in the database object.

In one example, the method may also include controlling the DBMS to instantiate the database object to include a set of metadata in which an assembly instruction can be stored. The set of metadata may store additional information. For example, the set of metadata may store a stream segment to be added to a version of the database object.

The example method may also include controlling the DBMS to instantiate the database object to include a second binary object. The second binary object may store an assembly instruction. The second binary object may also store a stream segment to be added to a version of the database object.

Figure 6:
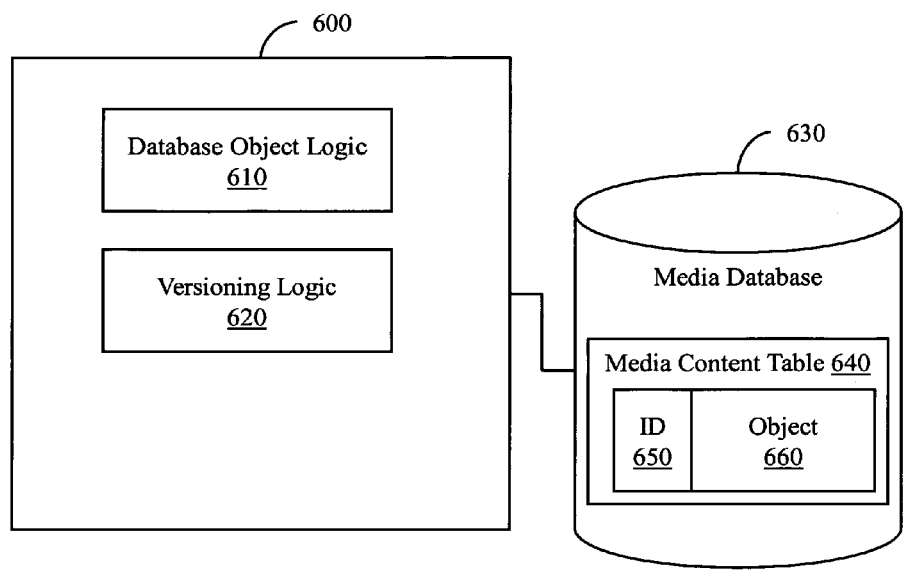
FIG. 6 illustrates an example system associated with persistent multimedia content storage with versioning.

FIG. 6 illustrates a system 600 that provides multimedia content versioning for a persistently stored database object. System 600 includes a database object logic 610. Logic 610 creates a database object 660 that is stored in a media content table 640 in a media database 630. The database object 660 includes a first binary large object (BLOB) attribute to store a multimedia content and a set of metadata attributes that describe the database object and/or the multimedia content. The multimedia content may be, for example, a medical image (e.g., MRI image). The database object 660 also includes an XML edits attribute that stores data describing edits made to the set of metadata attributes. In one example, the database object 660 may also include a second BLOB attribute that stores a second set of binary data. This second set of binary data may hold a binary mapping of a change to a member of the set of metadata attributes. Media content table 640 may store the object 660 and an identifier 650 associated with the object 660. Note how this differs from conventional systems where a media database may store metadata associated with a multimedia content but the multimedia content may actually be stored in an external storage location.

System 600 also includes a versioning logic 620. Versioning logic 620 provides versioning for the database object 660 stored in the media content table 640 in the media database 630. Versioning logic 620 may, upon determining that a member of the set of metadata attributes in object 660 has been changed, control the database object logic 610 to store data in the XML edits attribute of the database object 660 stored in the media content table 640 in the media database 630. The data stored by the database object logic 610 may include an editing entry associated with a change to a member of the set of metadata attributes. While system 600 is illustrated residing outside database 630, it is to be appreciated that in one example system 600 may itself be persistently stored in database 630.

Figure 7:
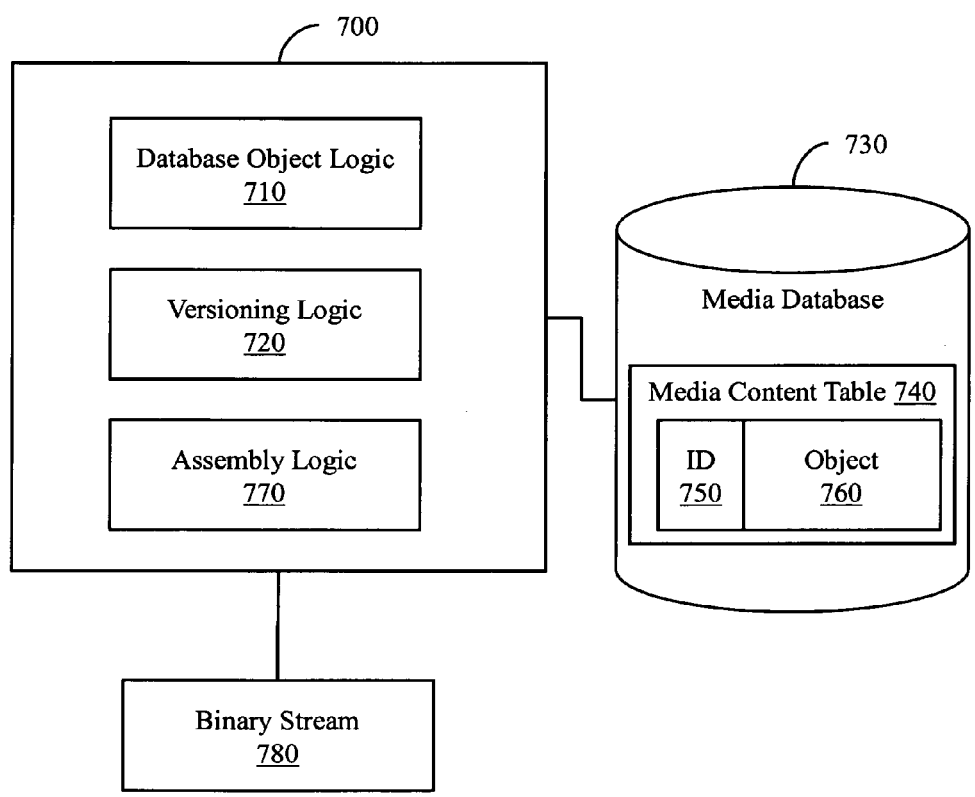
FIG. 7 illustrates another example system associated with persistent multimedia content storage with versioning.

FIG. 7 illustrates a system 700 that provides multimedia content versioning for a persistently stored database object. System 700 includes several elements similar to those described in connection with system 600 (FIG. 6). For example, system 700 includes a database object logic 710 and a versioning logic 720 that participate in persistently storing an object 760 in a media content table 740 in media database 730. The object 760 may have a related identifier 750 stored in the media content table 740. However, system 700 includes an additional logic.

System 700 includes an assembly logic 770 to provide a binary stream 780 that represents a selected version of the database object 760. In one example, the assembly logic 770 builds (e.g., assembles) the binary stream representing the selected version from data in object 760. For example, assembly logic 770 may build the binary stream 780 from the first set of binary data, the set of metadata attributes, the second set of binary data, and the XML edits attribute. Building the binary stream 780 may include identifying a base version of object 760, deletions from object 760, and additions and/or modifications to object 760. In one example, assembly logic 770 may be a stored procedure in a media database 730.

In one example, assembly logic 770 may compute:

$$BLOB(I+K)=BLOB(I)-U(I,K)+M(I,K)$$

Where:
BLOB(I) is the I-th version of the first set of binary data;
U(I,K) is a complete set of metadata attributes to be deleted from I-th version of the database object; and
M(I,K) represents a complete set of metadata attributes to be added to the i-th version of the database object.

The following derivation illustrates how a particular version of a media object may be assembled without requiring the assembly of intermediate versions. For example, a version 4 can be assembled directly from a version 1 without assembling version 2 and version 3, and vice versa.

$A_i$: A set of attributes to add to the metadata attributes of version i $D_i$: A set of attributes to delete from the metadata attributes of version i U(I,K): Complete set of attributes to be deleted from metadata of version I in order to change from version I into version K.

M(I,K): Complete set of attributes to be added to metadata of version I in order to change from version I to version K.

The following recursive function can be applied to update a BLOB attribute:

$$BLOB(i) := (BLOB(i-1) - D_i) + A_i.$$

if BLOB(i) stored, derive BLOB(i+1), BLOB(i+2) . . . and so on from it:

$$BLOB(i+1) := ((BLOB(i-1) - D_i) + A_i) - D_{i+1} + A_{i+1}$$
$$:= (BLOB(i-1) - D_i - D_{i+1}) + ((A_i - D_{i+1}) + A_{i+1})$$
$$:= (BLOB(i-1) - \text{Union}(D_i, D_{i+1})) + ((A_i - D_{i+1}) + A_{i+1})$$

...

$$BLOB(i+k) := (BLOB(i) - \text{Union}(D_{i+1}, \ldots D_{i+k})) +$$
$$(A_{i+1} - D_{i+2} + A_{i+2} - D_{i+3} \ldots - D_{i+k} + A_{i+k})$$

$$BLOB(i+k) = BLOB(I) - U(I, K) + M(I, K);$$

Where $U(I, K) := \text{Union}(D_{i+1}, \ldots D_{i+k})$ and $$M(I, K) := A_{i+1} - D_{i+2} + A_{i+2} - D_{i+3} \ldots - D_{i+k} + A_{i+k};$$

BLOB(i−1), BLOB(i−2) and so on can be derived similarly:

BLOB(i−1)=BLOB(i)−$A_i$+$D_i$
BLOB(i−2)=(BLOB(i)−$A_i$+$D_i$)−$A_{i-1}$+$D_{i-1}$
BLOB(i−k)=BLOB(i)−Union($A_i$, . . . $A_{i-k+1}$)+($D_i$−$A_i$+$D_{i-1}$+$A_{i-1}$+ . . . −$A_{i-k+1}$+$D_{i-k+1}$)

In one example, changes (e.g., deletions) between versions are constrained to include the complete attribute value, and not just attribute tag, in order to get back to an earlier version. Using this derivation, for a persistent object that stores the current version I of a multimedia object, for each version of media object K, U(I,K) and M(I,K) can be pre-computed and stored. Thus, some example systems and methods described herein store the stream descriptor representation of U(I,K) and M(I,K) in the extension attribute of the persistently stored database object. While system 700 is illustrated residing outside database 730, it is to be appreciated that in one example system 700 may itself be persistently stored in database 730.

Figure 8:
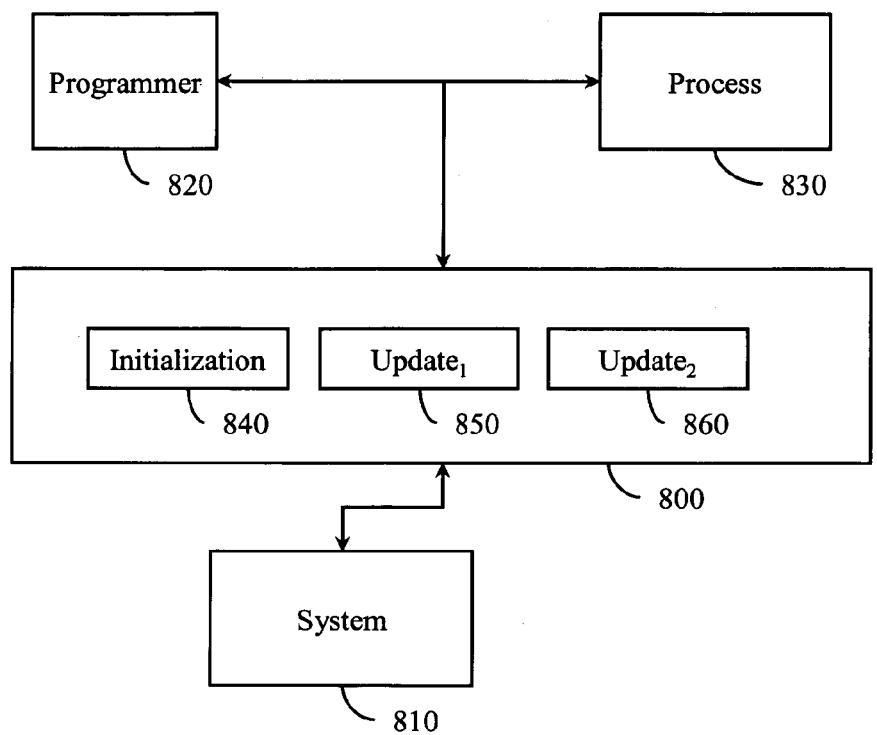
FIG. 8 illustrates an example Application Programming Interface (API) associated with persistent multimedia content storage with versioning.

FIG. 8 illustrates an application programming interface (API) 800 that provides access to a system 810 associated with providing persistent multimedia content versioning. The API 800 may be employed, for example, by a programmer 820 and/or a process 830 to gain access to processing performed by the system 810 and/or a functionally equivalent method. For example, the programmer 820 may write a program to access the system 810 (e.g., invoke its operation, monitor its operation, control its operation) where writing the program is facilitated by the presence of the API 800. Rather than the programmer 820 having to understand the internals of the system 810, the programmer 820 merely has to learn the interface to the system 810. This facilitates encapsulating the functionality of system 810 while exposing that functionality.

In one example, the API 800 may be stored on a computer-readable medium. The interfaces in the API 800 can include, but are not limited to, a first interface 840 that communicates information associated with initializing a persistent multimedia database object with a binary media and with XML metadata attributes. The interfaces may also include a second interface 850 that communicates information associated with updating a persistent multimedia database object from a first previous version to a second version. The interfaces may also include a third interface 860 that communicates information associated with updating a persistent multimedia database object so that a specified version of the persistent multimedia database object is stored.

Figure 9:
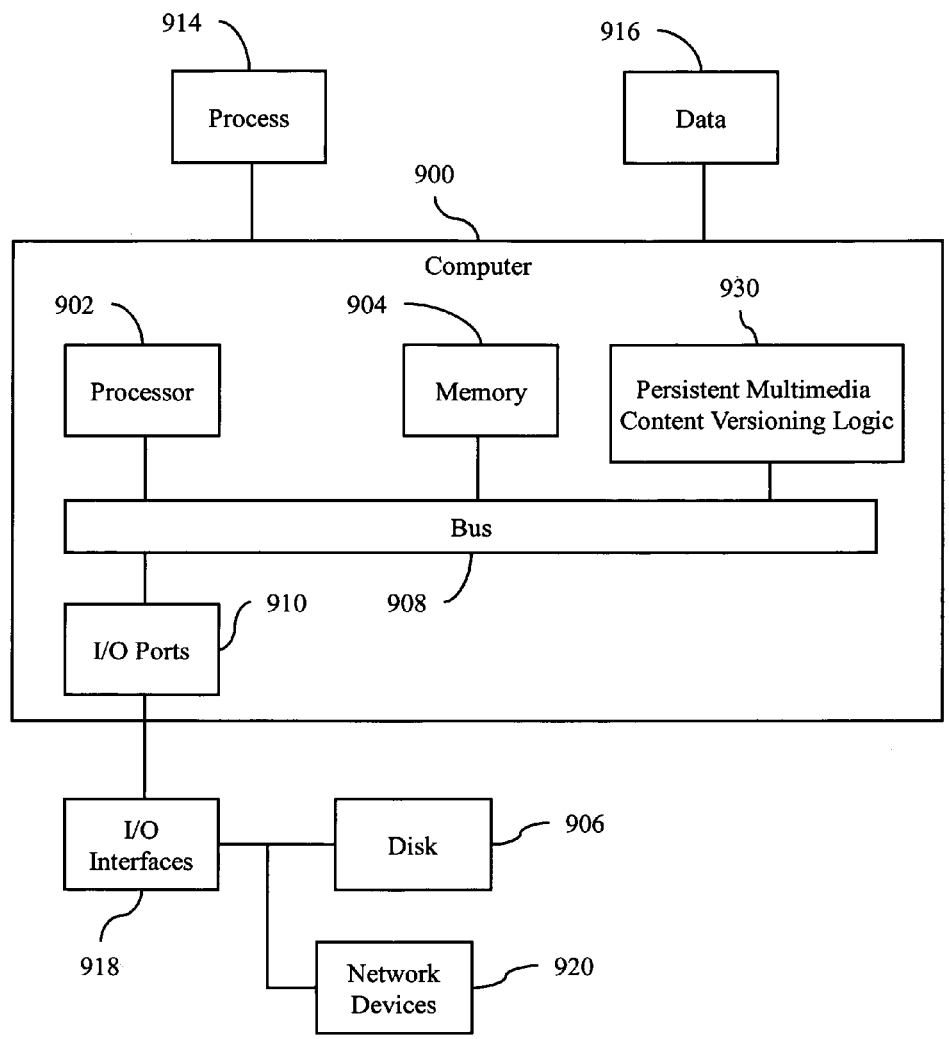
FIG. 9 illustrates an example computing environment in which example systems and methods, and equivalents, may operate.

FIG. 9 illustrates an example computing device in which example systems and methods described herein, and equivalents, may operate. The example computing device may be a computer 900 that includes a processor 902, a memory 904, and input/output ports 910 operably connected by a bus 908. In one example, the computer 900 may include a persistent multimedia content versioning logic 930 configured to provide content versioning for a multimedia object. In different examples, the logic 930 may be implemented in hardware, software, firmware, and/or combinations thereof. While the logic 930 is illustrated as a hardware component attached to the bus 908, it is to be appreciated that in one example, the logic 930 could be implemented in the processor 902.

Thus, logic 930 may provide means (e.g., hardware, software, firmware) for instantiating a persistent database object. The persistent database object may include, for example, a first binary large object (BLOB) attribute to store a multimedia content, a set of metadata attributes that describe the database object and/or the multimedia content, an XML edits attribute to store an edit to the set of metadata attributes, and a second BLOB attribute to store a second set of binary data associated with a binary mapping of a change to a member of the set of metadata attributes. The logic 930 may also include means for updating the XML edits attribute in response to detecting an edit of a member of the set of metadata attributes. For example, when a metadata attribute is deleted, a metadata attribute is added, a metadata attribute value is changed, and so on, these manipulations may be detected and logic 930 may update the XML edits attribute to capture information describing the manipulation. Logic 930 may also include means for providing a binary stream representing a version of the persistent database object. The version may be synthesized from data stored in the first BLOB, data stored in the set of metadata attributes, and data stored in the XML edits attribute.

The means may be implemented, for example, as an ASIC programmed to control processor 902 with respect to processing data 916. The means may also be implemented as computer executable instructions that are presented to computer 900 as data 916 that are temporarily stored in memory 904 and then executed by processor 902.

Generally describing an example configuration of the computer 900, the processor 902 may be a variety of various processors including dual microprocessor and other multiprocessor architectures. A memory 904 may include volatile memory and/or non-volatile memory. Non-volatile memory may include, for example, ROM, PROM, and so on. Volatile memory may include, for example, RAM, SRAM, DRAM, and so on.

A disk 906 may be operably connected to the computer 900 via, for example, an input/output interface (e.g., card, device) 918 and an input/output port 910. The disk 906 may be, for example, a magnetic disk drive, a solid state disk drive, a floppy disk drive, a tape drive, a Zip drive, a flash memory card, a memory stick, and so on. Furthermore, the disk 906 may be a CD-ROM drive, a CD-R drive, a CD-RW drive, a DVD ROM, and so on. The memory 904 can store a process 914 and/or a data 916, for example. The disk 906 and/or the memory 904 can store an operating system that controls and allocates resources of the computer 900.

The bus 908 may be a single internal bus interconnect architecture and/or other bus or mesh architectures. While a single bus is illustrated, it is to be appreciated that the computer 900 may communicate with various devices, logics, and peripherals using other busses (e.g., PCIE, 1394, USB, Ethernet). The bus 908 can be types including, for example, a memory bus, a memory controller, a peripheral bus, an external bus, a crossbar switch, and/or a local bus.

The computer 900 may interact with input/output devices via the i/o interfaces 918 and the input/output ports 910. Input/output devices may be, for example, a keyboard, a microphone, a pointing and selection device, cameras, video cards, displays, the disk 906, the network devices 920, and so on. The input/output ports 910 may include, for example, serial ports, parallel ports, and USB ports.

The computer 900 can operate in a network environment and thus may be connected to the network devices 920 via the i/o interfaces 918, and/or the i/o ports 910. Through the network devices 920, the computer 900 may interact with a network. Through the network, the computer 900 may be logically connected to remote computers. Networks with which the computer 900 may interact include, but are not limited to, a LAN, a WAN, and other networks.

Figure 10:
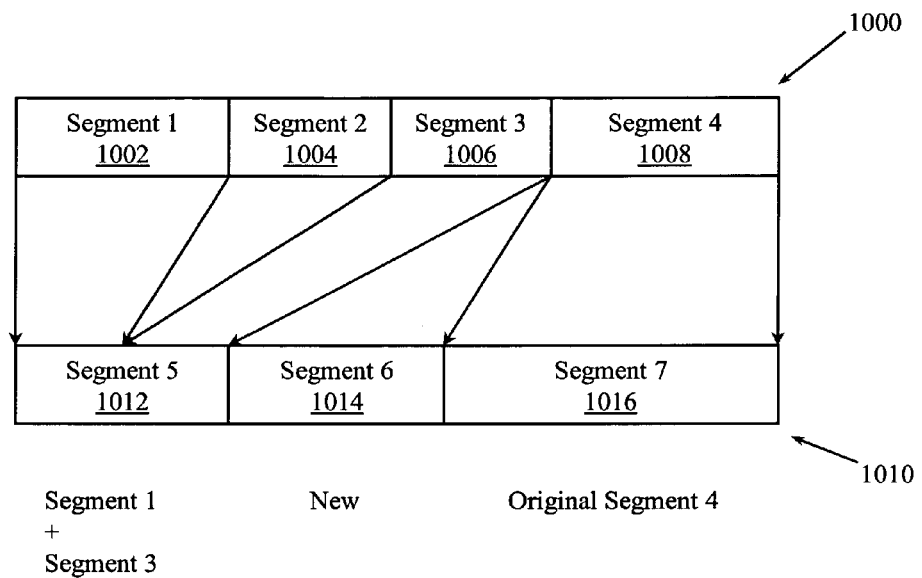
FIG. 10 illustrates a binary stream being assembled from binary data associated with a multimedia content and a set of pre-computed binary segments that may be stored in the extension attribute of a database object.

FIG. 10 illustrates a binary stream 1010 being assembled from a first set of binary data 1000. The binary stream 1010 may be assembled using the example methods and/or systems described above. In one example, binary stream segments 1012, 1014, and 1016 may be pre-computed and stored in the extension attribute of a database object. Assembly instructions may be stored as a group of tuples. A tuple may include, for example, one Boolean number followed by two long types. In one example, the assembly instructions may be stored in an extension BLOB. In another example, the assembly instructions may be encoded in XML and saved in a metadata attribute of a media object.

Data 1000 corresponds to one version of a multimedia object. Stream 1010 corresponds to a different version that can be assembled from data 1000 and edit information stored in the same object as data 1000. Recall that changes (e.g., attribute deletions, attribute additions, attribute modifications) to the version represented by data 1000 can be mapped into binary operations on the binary stream 1010. A set of deletes that remove consecutive bytes can be gathered together as deleting a stream segment (e.g., remove segment2 1004 from data 1000). A set of insertions that add consecutive bytes can be gathered together as adding a stream segment (e.g., add segment6 1014 to stream 1010).

Thus, a new version of a multimedia object associated with 1000 can be provided in binary stream 1010. The new version can be described as a set of stream descriptors that map the segments of stream 1010 to data 1000. In the case of additions, additional stream segments may be included. In the example illustrated in FIG. 10, the version represented by stream 1010 may be described as:

Segment1 (M, offset1, length1)
Segment3 (M, offset3, length3)
Segment6 (E, offset6, length6)
Segment7 (M, offset4, length4)

Where M indicates that the source of the stream segment is data 1000 (which is stored in the first BLOB attribute of a database object) and E indicates that the source of the stream segment is the extension attribute of the database object. In one example, extension attributes may be managed as fixed-size, strongly-typed binary blocks having a header block to store pointers. The pointers may facilitate jumping directly to a specific version.

Thus FIG. 10 illustrates two different versions of a binary stream associated with a multimedia content and how one is built from the other. The binary stream 1010 can be built using a stream oriented interface that starts with a previous version (e.g., data 1000) and builds new version 1010 one stream segment at a time during an "assembly". Insertion segments can be stored in the extension ($2^{nd}$ BLOB) attribute of a database object so that they are co-located with the persistently stored content 1000. The XML edits attribute store data (e.g., instructions) associated with the copies, deletes, inserts, and so on. The instructions may be stream based and thus may include segment numbers, offsets, and lengths. The second version (e.g., stream 1010) can be assembled by starting at the first version (e.g., data 1000) and applying the instructions in the XML edits attribute to cause a stream based assembly. While medical images have been described, it is to be appreciated that this stream based assembly may be applied to other segmented streams, not just multimedia content associated with medical images.

While example systems, methods, and so on, have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and so on, described herein. Therefore, the invention is not limited to the specific details, the representative apparatus, and illustrative examples shown and described. Thus, this application is intended to embrace alterations, modifications, and variations that fall within the scope of the appended claims.

To the extent that the term "includes" or "including" is employed in the detailed description or the claims, it is intended to be inclusive in a manner similar to the term "comprising" as that term is interpreted when employed as a transitional word in a claim.

To the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

To the extent that the phrase "one or more of, A, B, and C" is employed herein, (e.g., a data store configured to store one or more of, A, B, and C) it is intended to convey the set of possibilities A, B, C, AB, AC, BC, and/or ABC (e.g., the data store may store only A, only B, only C, A&B, A&C, B&C, and/or A&B&C). It is not intended to require one of A, one of B, and one of C. When the applicants intend to indicate "at least one of A, at least one of B, and at least one of C", then the phrasing "at least one of A, at least one of B, and at least one of C" will be employed.

What is claimed is:

1. A non-transitory computer-readable medium storing computer-executable instructions, the non-transitory computer-readable medium comprising instructions for:
controlling a database management system (DBMS) to generate a database object comprising a first binary large object (BLOB) attribute, an XML edits attribute, and a set of metadata attributes;
storing a first set of binary data associated with a multimedia content in the first BLOB attribute;

storing one or more values in the set of metadata attributes, where the one or more values are associated with one or more of, the multimedia content, and the database object;
controlling the DBMS to store the database object in a column in a table in a relational database managed by the DBMS; and
storing in the XML edits attribute an editing entry that describes a change to the database object, where the XML edits attribute includes a plurality of editing entries that describe a history of changes to values of the set of metadata attributes and the multimedia content;
upon determining that the database object has changed, storing in the XML edits attribute an editing entry associated with the change, wherein the editing entry describes the change to the database object and includes content associated with the change,
wherein the editing entry includes one or more of, an addition to the set of metadata attributes, and an update to the set of metadata attributes;
storing in a second BLOB attribute one or more of, a set of binary data associated with an addition to the set of metadata attributes, and a set of binary data associated with an update to the set of metadata attributes; and
providing a binary stream that represents a selected version of the database object by computing the selected version from a current version of the database object and the plurality of editing entries, wherein the selected version is generated by deleting a differential set of metadata attributes from the current version and adding a missing set of metadata attributes to form the selected version, wherein the missing set of metadata attributes are retrieved from the second BLOB attribute.

2. The computer-readable medium of claim 1, wherein the plurality of editing entries permit storing a plurality of versions of the database object without storing multiple separate copies of the database object, and wherein the plurality of editing entries permit restoring a selected version of the database object from a previous point in time without restoring intermediate versions of the database object.

3. The computer-readable medium of claim 2, where the editing entry describes a deletion from the set of metadata attributes.

4. The computer-readable medium of claim 2, where the editing entry describes a deletion from the first set of binary data.

5. The computer-readable medium of claim 1, where the database object includes a second BLOB attribute to store a second set of binary data associated with a binary mapping of a change to a member of the set of metadata attributes.

6. The computer-readable medium of claim 5, where the second set of binary data is also associated with a binary mapping of a change to the first set of binary data.

7. The computer-readable medium of claim 6, where the editing entry includes one or more of, an addition to the first set of binary data, and an update to the first set of binary data.

8. The computer-readable medium of claim 7, further comprising instructions for storing in the second BLOB attribute one or more of, a set of binary data associated with an addition to the first set of binary data, and a set of binary data associated with an update to the first set of binary data.

9. The computer-readable medium of claim 1, further comprising instructions for controlling the DBMS to produce an index for the XML edits attribute.

10. The computer-readable medium of claim 9, where the instructions for controlling the DBMS to produce the index includes instructions for controlling the DBMS to produce an index associated with XMLIndex.

11. The computer-readable medium of claim 10, further comprising instructions for performing one or more of, providing a result to a keyword query directed at the XML edits attribute, and providing a result to an XPATH query directed at the XML edits attribute, where the result is based, at least in part, on the index.

12. The computer-readable medium of claim 1, where the database object is a PL/SQL object.

13. The computer-readable medium of claim 1, further comprising instructions for:
pre-computing a difference between a first version of the set of metadata attributes and a second different version of the set of metadata attributes; and
storing the difference as a set of binary data in the second BLOB attribute.

14. The computer-readable medium of claim 1, further comprising instructions for: computing a binary mapping associated with an edit entry in the XML edits attribute and storing the binary mapping as a set of binary data in the second BLOB attribute.

15. The computer-readable medium of claim 1, where the first set of binary data represents a medical image.

16. The computer-readable medium of claim 1, where data concerning a change to a member of the set of metadata attributes is to be stored in the set of metadata attributes.

17. The computer-readable medium of claim 16, where an object assembly instruction is to be derived based, at least in part, on one or more editing entries stored in the XML edits attribute.

18. A computing system, comprising:
a database object logic to create a database object comprising a first binary large object (BLOB) attribute to store a multimedia content, a set of metadata attributes that describe one or more of, the database object, and the multimedia content, an XML edits attribute to store a set of edits that describe a history of changes to values of the set of metadata attributes and the multimedia content, and a second BLOB attribute to store a second set of binary data associated with a binary mapping of a change to a member of the set of metadata attributes; and
a non-transitory computer-readable medium comprising a versioning logic to provide versioning for the database object, where providing versioning for the database object includes, upon determining that a member of the set of metadata attributes has been changed, controlling the database object logic to store in the XML edits attribute an editing entry associated with a change to a member of the set of metadata attributes,
wherein the versioning logic is configured to store in the XML edits attribute an editing entry associated with the change, wherein the editing entry describes the change to the database object and includes content associated with the change,
wherein the editing entry includes one or more of, an addition to the set of metadata attributes, and an update to the set of metadata attributes,
wherein the versioning logic is configured to store in the second BLOB attribute one or more of, a set of binary data associated with an addition to the set of metadata attributes, and a set of binary data associated with an update to the set of metadata attributes; and
an assembly logic configured to provide a binary stream that represents a selected version of the database object by computing the selected version from a current version of the database object and the plurality of editing entries, wherein the selected version is generated by deleting a differential set of metadata attributes from the current version and adding a missing set of metadata attributes to form the selected version, wherein the missing set of metadata attributes are retrieved from the second BLOB attribute.

19. A set of application programming interfaces embodied on a non-transitory computer-readable medium for execution by a computer component in conjunction with providing persistent multimedia content versioning for a persistent multimedia database object, comprising:

a first interface to communicate electronic information that causes the computer component to initialize the persistent multimedia database object having a binary media, XML metadata attributes, and an XML edits attribute that includes a set of edits that describe a history of changes to values of the persistent multimedia database object, where the persistent multimedia database object is stored in a single column of a database in a storage device and comprises a first binary large object (BLOB) attribute;

a second interface to communicate electronic information that causes the computer component to update the persistent multimedia database object from a first previous version to a second version; and a third interface to communicate electronic information that causes the computer component to update the persistent multimedia database object so that a specified version of the persistent multimedia database object is stored in the storage device, wherein the third interface is configured to store in the XML edits attribute an editing entry associated with a change to the persistent multimedia database object, wherein the editing entry describes the change to the persistent multimedia database object and includes content associated with the change, wherein the editing entry includes one or more of, an addition to the XML metadata attributes, and an update to the XML metadata attributes, wherein the third interface is configured to store in a second BLOB attribute one or more of, a set of binary data associated with an addition to the XML metadata attributes, and a set of binary data associated with an update to the XML metadata attributes, and wherein the third interface is configured to provide a binary stream that represents a selected version of the persistent multimedia database object by computing the selected version from a current version of the persistent multimedia database object and the XML edits attribute, wherein the selected version is generated by deleting a differential set of XML metadata attributes from the current version and adding a missing set of XML metadata attributes to form the selected version, wherein the missing set of XML metadata attributes are retrieved from the second BLOB attribute.

20. A non-transitory computer-readable medium storing computer-executable instructions, the computer-executable instructions comprising instructions for:

storing a data object comprising a first binary large object (BLOB) in a database, where the data object comprises:
  a first storage area containing data representing an image;
  a second storage area containing metadata describing the image; and
  a third storage area containing edits that are changes to values of the metadata and the image, where the edits include a plurality of changes to the metadata and the image that describe an editing history of the metadata and the image;

updating the edits in response to a change in the metadata where updating the edits includes storing instructions associated with one or more of a copy, a delete, and an insert, wherein the edits describe the change to the database object and includes content associated with the change, wherein the edits includes one or more of, an addition to the metadata, and an update to the metadata, wherein the content of the change is stored in a second BLOB; and selectively restoring, to a non-transitory computer-readable medium, a selected version of the object by synthesizing the version from the data representing the image, the metadata, and the edits to the metadata, wherein selectively restoring the selected version includes providing a binary stream that represents the selected version of the database object by computing the selected version from a current version of the database object and the edits, wherein the selected version is generated by deleting a differential set of metadata from the current version and adding a missing set of metadata to form the selected version, wherein the missing set of metadata are retrieved from the second BLOB.

21. A system, comprising:

means for instantiating a persistent database object having a first binary large object (BLOB) attribute to store a multimedia content, a set of metadata attributes that describe the database object and the multimedia content, an XML edits attribute to store an edit to the set of metadata attributes and the multimedia content, and a second BLOB attribute to store a second set of binary data associated with a binary mapping of a change to a member of the set of metadata attributes;

means for updating the XML edits attribute in response to detecting an edit of a member of the set of metadata attributes, where the means for updating includes at least one non-transitory computer-readable medium and where the XML edits attribute include a plurality of changes of values of the set of metadata and the multimedia content to maintain an editing history of the persistent multimedia content, wherein the means for updating include means for storing in the XML edits attribute an editing entry associated with the edit, wherein the editing entry describes the edit to the persistent database object and includes content associated with the edit, wherein the editing entry includes one or more of, an addition to the set of metadata attributes, and an update to the set of metadata attributes, wherein the means for updating the XML edits attribute include means for storing in the second BLOB attribute one or more of, a set of binary data associated with an addition to the set of metadata attributes, and a set of binary data associated with an update to the set of metadata attributes; and means for providing a binary stream representing a selected version of the persistent database object based, at least in part, on data stored in the first BLOB, data stored in the set of metadata attributes, and data stored in the XML edits attribute by computing the selected version from a current version of the persistent database object and the XML edits attribute, wherein the selected version is generated by deleting a differential set of metadata attributes from the current version and adding a missing set of metadata attributes to form the selected version, wherein the missing set of metadata attributes are retrieved from the second BLOB attribute.

22. A non-transitory computer-readable medium storing computer-executable instructions, the non-transitory computer-readable medium comprising instructions for:

controlling a database management system (DBMS) to create a database object comprising a first binary large object (BLOB) attribute, and a versions attribute;

storing a first set of binary data associated with a multimedia content in the first BLOB attribute;

storing values in the versions attribute, where the values describe changes to values of the multimedia content, and the database object to maintain an editing history of the multimedia content and the database object; and controlling the DBMS to store the database object in a column in a table in a relational database managed by the DBMS;

upon determining that the database object has changed, storing in the versions attribute an editing entry associated with a change, wherein the editing entry describes the change to the database object and includes content associated with the change, wherein the editing entry includes one or more of, an addition to database object, and an update to the database object;

storing in a second BLOB attribute one or more of, a set of binary data associated with an addition to the database object, and a set of binary data associated with an update to the database object; and providing a binary stream that represents a selected version of the database object by computing the selected version from a current version of the database object and the editing history of the versions attribute, wherein the selected version is generated by deleting a differential set of changes to the database object from the current version and adding a missing set of changes to the database object to form the selected version, wherein the missing set of changes are retrieved from the second BLOB attribute.

23. The computer-readable medium of claim 22, where the versions attribute stores one or more assembly instructions from which a version of the binary object can be computed.

24. The computer-readable medium of claim 23, further comprising instructions for controlling the DBMS to store in the database object one or more binary streams added to the database object.

25. The computer-readable medium of claim 23, where the assembly instructions include a delete instruction that identifies a segment of the binary data associated with the multimedia content to be excluded from a version.

26. The computer-readable medium of claim 25, where the assembly instructions include an addition instruction that identifies a segment of binary data to be added to the binary data associated with the multimedia content.

27. The computer-readable medium of claim 26, where the assembly instructions include a copy instruction that identifies a segment of binary data to be copied from the binary data associated with the multimedia content when a version of the multimedia content is assembled.

28. The computer-readable medium of claim 23, further comprising instructions for controlling the DBMS to instantiate the database object to include a set of metadata in which an assembly instruction can be stored.

29. The computer-readable medium of claim 28, further comprising instructions for controlling the DBMS to store in the set of metadata a stream segment to be added to a version of the database object.

30. The computer-readable medium of claim 23, further comprising instructions for controlling the DBMS to instantiate the database object to include a second binary object in which an assembly instruction can be stored.

31. The computer-readable medium of claim 30, further comprising instructions for controlling the DBMS to store in the second binary object a stream segment to be added to a version of the database object.

* * * * *

UNITED STATES PATENT AND TRADEMARK OFFICE
CERTIFICATE OF CORRECTION

PATENT NO.        : 9,058,407 B2
APPLICATION NO.   : 12/009750
DATED             : June 16, 2015
INVENTOR(S)       : Guo It is certified that error appears in the above-identified patent and that said Letters Patent is hereby corrected as shown below:

Specification

In column 3, line 36, delete "may by" and insert -- may be --, therefor.

In column 13, line 4, after "i" insert -- . --.

In column 13, line 6, after "i" insert -- . --.

Signed and Sealed this
Eighth Day of March, 2016

Michelle K. Lee
*Director of the United States Patent and Trademark Office*